United States Patent [19]
McDonald

[11] Patent Number: 5,776,192
[45] Date of Patent: Jul. 7, 1998

[54] ARTIFICIAL LENS INSERTIBLE BETWEEN THE IRIS AND NATURAL LENS OF THE EYE

[75] Inventor: Henry H. McDonald, Pasadena, Calif.

[73] Assignee: Surgical Concepts, Inc. Newport Beach, Calif.

[21] Appl. No.: 622,104

[22] Filed: Mar. 26, 1996

Related U.S. Application Data

[62] Division of Ser. No. 229,793, Apr. 19, 1994, abandoned.

[51] Int. Cl.$^6$ ........................................... A61F 2/16
[52] U.S. Cl. ........................................... 623/6
[58] Field of Search ........................................... 623/6

[56] References Cited

U.S. PATENT DOCUMENTS

| | | | |
|---|---|---|---|
| 4,573,998 | 3/1986 | Mazzocco | 623/6 |
| 4,585,456 | 4/1986 | Blackmore | 623/6 |
| 4,731,078 | 3/1988 | Stoy et al. | 623/6 |
| 4,759,761 | 7/1988 | Portnoy | 623/6 |
| 4,769,035 | 9/1988 | Kelman | 623/6 |
| 4,813,957 | 3/1989 | McDonald | 623/6 |
| 4,840,627 | 6/1989 | Blumenthal | 123/6 |
| 4,888,014 | 12/1989 | Nguyen | 623/6 |
| 4,907,586 | 3/1990 | Bille et al. | 606/5 |
| 4,932,970 | 6/1990 | Portney | 623/6 |
| 4,957,505 | 9/1990 | McDonald | 623/6 |
| 4,959,070 | 9/1990 | McDonald | 623/6 |
| 5,019,097 | 5/1991 | Knight et al. | 623/5 |
| 5,030,231 | 7/1991 | Portney | 623/6 |
| 5,044,743 | 9/1991 | Ting | 623/6 X |
| 5,098,444 | 3/1992 | Feaster | 623/6 |
| 5,203,789 | 4/1993 | McDonald | 623/6 |
| 5,203,790 | 4/1993 | McDonald | 623/6 |
| 5,292,324 | 3/1994 | Mcdonald | 623/6 |

FOREIGN PATENT DOCUMENTS

| | | | |
|---|---|---|---|
| 2666735 | 3/1992 | France | 623/6 |
| WO8902252 | 3/1989 | WIPO | 623/6 |
| WO9113597 | 9/1991 | WIPO | 623/6 |
| 9220302 | 11/1992 | WIPO | 623/6 |

Primary Examiner—Mary Beth Jones
Attorney, Agent, or Firm—William W. Haefliger

[57] ABSTRACT

An artificial soft lens insertable into the eye between the iris and the natural lens comprising the lens being compliant and having opposed surfaces: the lens configured to flex under pressure exerted by the iris whereby at least one of the opposed surfaces yieldably and resiliently deforms.

7 Claims, 5 Drawing Sheets

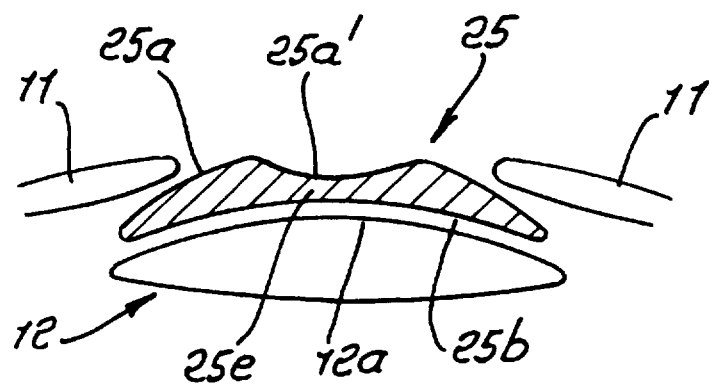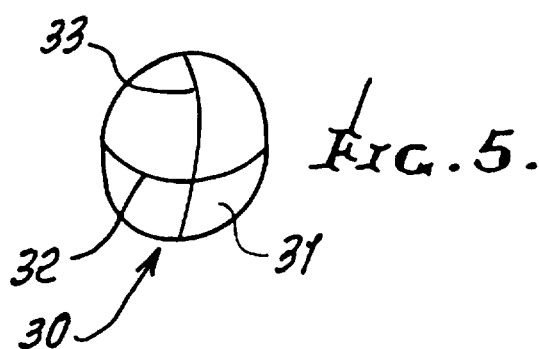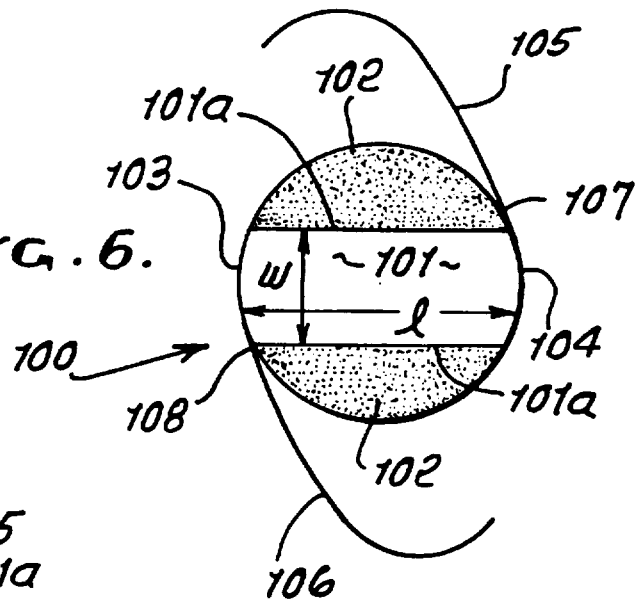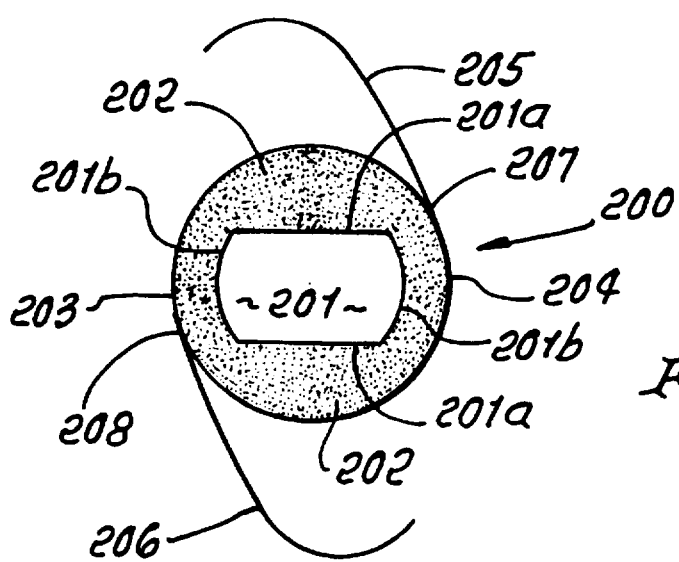

ARTIFICIAL LENS INSERTIBLE BETWEEN THE IRIS AND NATURAL LENS OF THE EYE

This is a division of application Ser. No. 08/229,793, filed Apr. 19, 1994, now abandoned.

BACKGROUND OF THE INVENTION

This invention relates generally to improved lens implants useful in primary and secondary cataract extractions, and also useful in intraocular contact lens implantations.

There is need for improvements in lens implants and procedures to enable savings in surgical time and cost, as well as reduction in use of expensive materials, medications, convalescence time, and reduction in post-operative physical restrictions leading to almost immediate return to practical vision. There is also need for very small lens implants enabling employment of correspondingly very small surgical wounds without need for sutures, and practical elimination of pain associated with surgery.

SUMMARY OF THE INVENTION

It is a major object of the invention to provide an improved lens implant meeting the above need or needs. Basically, the artificial soft lens of the invention is insertible into the eye through a very small incision, and to a position between the natural lens and the iris, that lens being compliant and having opposed surfaces, the lens configured to flex under pressure exerted by the iris whereby at least one of the opposed surfaces yieldably and resiliently deforms. The lens is typically aspherical.

Additional objectives include the provision of an aspherical lens; one of whose surfaces is convex and the other surface being concave; the other surface may have generally the same curvature (concave) as a convex surface defined by the eye natural lens, and which is engageable by the artificial lens concave surface.

Yet another object is the provision of a small lens, as referred to, and having a haptic or haptics integral with the lens at an edge portion or portions thereof. Such haptics may be tabular, and the lens elongated between the haptics.

Another object is the provision of a lens, as referred to, having an interior cavity, which is typically hollow. Such a lens typically has opposed exterior convex surfaces, and opposed interior concave surfaces at opposite sides of the cavity.

An additional object is the provision of a lens having one exterior surface which is concave, for presentation toward the natural lens of the eye, and having another exterior surface with a central portion, which is concave, and an outer portion which is convex.

The invention is compatible with the latest improvements in lens implant techniques used not only in primary and secondary cataract extractions, but also conceivably useful in the most recent intraocular contact lens implantations.

The lens improvements are useful, novel, practical, and cost effective, as will be seen, in achieving savings in surgical time, reductions in the use of expensive materials, medications, convalescence in the recovery room, as well as reductions in physical restrictions, post-operatively, enabling an almost immediate return to practical vision, without pain or undue anxiety, these being of important advantage to patients.

The invention enables employment of a very small surgical wound in the eye, and through which implantations can be achieved. Small wound sizes of not only 3 mm but down to 2.5 to 2.0 mm. are enabled, depending upon whether the silicon lens implant is folded or non-folded. Such smallness in the wound size eliminates need for sutures; and lens surgery is required, since surgical manipulations become unnecessary. For example, no cautery and no conjunctival flaps are required, only topical anesthetics are employed. Further, no anesthetics, no injections, and no needles or expensive pharmaceuticals are needed during short time interval (ten minutes or so) cataract extraction and lens implant; and during very short time interval (five minutes or so) intraocular contact lens implantations.

New methods of lens implantation are also disclosed and claimed herein.

These and other objects and advantages of the invention, as well as the details of an illustrative embodiment, will be more fully understood from the following specification and drawings, in which:

DRAWING DESCRIPTION

FIG. 4 is a view like FIG. 1 showing a further modified artificial lens in position;

FIG. 5 is a view showing an artificial lens, in perspective, the lens having different curvatures, in perpendicular intersecting planes;

FIG. 6 is a plan view of a lens, with darkened areas;

FIG. 7 is a plan view of another lens, with darkened areas;

DETAILED DESCRIPTION

Figure 1:
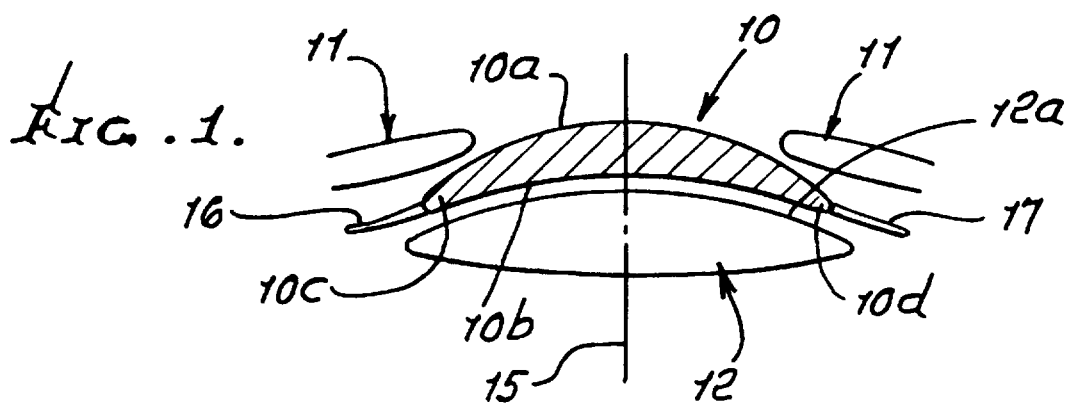
FIG. 1 is a view taken in section through the eye, showing positioning of an artificial lens adjacent a vertical lens.

In FIG. 1, an artificial, soft lens 10, as for example of silicone, has been inserted into the eye between the iris 11 and the natural lens 12. Lens 10 is compliant and has opposed surfaces 10a and 10b. The lens is configured to flex under pressure, exerted by the iris toward the natural lens; the lens outer, thinner portions 10c and 10d engaged by the iris being particularly subject to flexing, to conform to the iris and to the convex surface 12a of the natural lens engaged by the artificial lens. Accordingly, at least one of the opposed surfaces 10a and 10b yieldably and resiliently deform.

Figure 2:
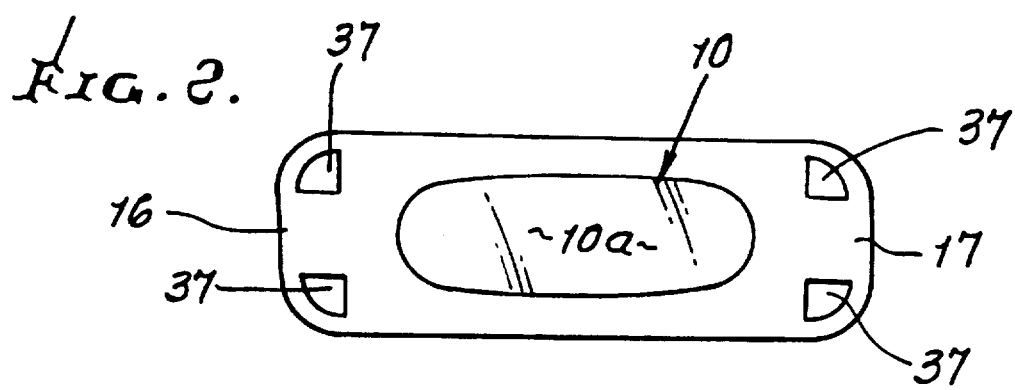
FIG. 2 is a view showing the artificial lens of FIG. 1 in plan view.

Lens 10 has aspherical configuration and may be elongated, as seen in FIG. 2. Surface 10a is convex and surface 10b is concave. The curvature of surface 10b may be generally the same as that of the convex surface 12a of the vertical lens 12, engaged by surface 10b. Also, surface 10a has greater curvature than that of surface 10b, at least in the plane of FIG. 1, which bisects the lenses 10 and 12, and which contains the lens axis 15.

FIGS. 1 and 2 shows two tabular-shaped haptics 16 and 17 integral with lens 10, to extend beneath the iris sections illustrated, the haptics intended to maintain the lens 10 in centered position. Portions of the haptics seen at 37 may comprise through holes into which eye tissue may grow, for acting to permanently position the haptics and artificial lens.

FIG. 3 again shows the natural lens 12 and iris segments 11. The artificial, soft lens 17 in this view defines an interior cavity 18 which is hollow, aiding the resiliently yieldable deformability of that lens. Also, one lens size for all diopters is enabled. The lens 17 has oppositely facing exterior convex surfaces 17a and 17b, and opposed concave interior surfaces 17c and 17d, at opposite sides of the cavity 18. Tabular haptics 20 and 21, like those of FIG. 2, integral with lens edge portions 17e and 17f, extend or project between the iris section 11 and the natural lens 12, as shown. The lens surface 17b has a central portion 17b', which contacts the central surface portion 12a' of the natural lens.

In FIG. 4, the natural lens 12 and iris segments 11 remain the same. The artificial, soft lens 25 in this view has a lower surface 25b that is concave to correspond in curvature, generally to the curvature of the natural lens upper surface 12a. The upper surface 25a of lens 25 has a central portion 25a', which is downwardly concave, i.e., sunk toward surface 25b. Accordingly, the central portion 25e of lens 25 is thinned. The laterally outer surface portion or portions 25a" is or are convex, upwardly, as shown, and project between the iris segments 11 and the natural lens.

Figure 3:
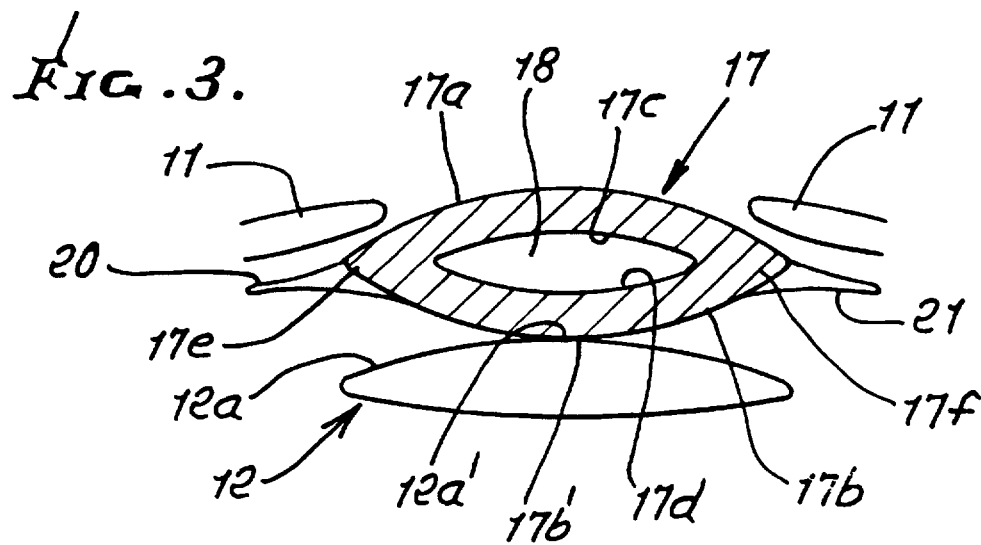
FIG. 3 is a view like FIG. 1 showing a modified artificial lens adjacent a natural lens.

FIG. 5 shows in perspective a representative soft lens 30, which may represent any of the lenses discussed but particularly the lenses of FIGS. 1 and 3. Its outer surface 31 (corresponding to surface 10a in FIG. 1 and to surface 17a in FIG. 3) has differential maximum and minimum curvature, one curvature (the maximum) defined by intersection 32, with surface 31 of a first plane containing the lens axis; and the other curvature (the minimum) defined by intersection 33 with surface 32 of a second plane containing the lens axis. Those two planes are normal to one another. This shows that soft lenses, as defined in FIGS. 1–4, can be molded to correct for astigmatism.

FIG. 6 shows an artificial soft lens 100, as for example of silicone, which may have the characteristics and utility of any of the lenses of FIGS. 1–5. Additionally, it has a medial transparent zone 101 and darkened or occluded border zones 102 adjacent opposite elongated edges 101a of zone 101. The latter is horizontally elongated between lens edges 103 and 104, and is larger that it is wide. Length and width dimensions "l" and "w" may be as follows:

l=6 mm w=3 mm

The lens is generally circular in outline, as shown, and may have a diameter of about 6 mm. Zone 101 is light passing; and zones 102 are light blocking. See also my U.S. Pat. Nos. 5,203,789 and 5,203,790 incorporated herein by reference.

Lens positioning haptics 105 and 106 are attached to the lens at opposite locations 107 and 108, and extend as shown. The lens can be folded and inserted into the eye via a 3 mm slit, as via the forceps disclosed in my U.S. Pat. Nos. 4,813,957 and 5,292,324. The lens can be made even smaller, if desired. The method of interocular emplacement of such artificial soft lens includes the steps:

a) providing the lens to have compliance and opposed surfaces, b) and inserting the lens between the iris and natural lens of the eye, so that one of the opposed surfaces stably engages the natural lens.

FIG. 7 shows another, or modified, artificial soft lens 200, as for example of silicone, which may also have the characteristics and utility of any of the lenses of FIGS. 1–5. Additionally, it has a medial transparent zone 201, and darkened or occluded border zones 202 adjacent opposite elongated edges 201a of zone 201. The latter is horizontally elongated between end edges 201b spaced inwardly from lens edges 203 and 204. Zone 201 is larger laterally than it is wide vertically. Length and width dimensions "l" and "w" may be as follows:

l=5 mm w=2.5 mm

The lens is generally circular in outline, as shown, and may have a diameter of about 6 mm. Haptics 205 and 206 are attached at their inner ends to the lens at opposite locations 207 and 208; and they extend outwardly as shown. The lens can be folded and inserted into the eye via a 3 mm slit, as via forceps referenced above. The lens can be made even smaller and inserted via a slit in the eye less than 3 mm in length. Lens discomfort and quicker surgery therefore result.

Zones 101 and 102 are zones of keener vision. The haptics, as shown, prevent lens rotation in the eye.

Figure 8:
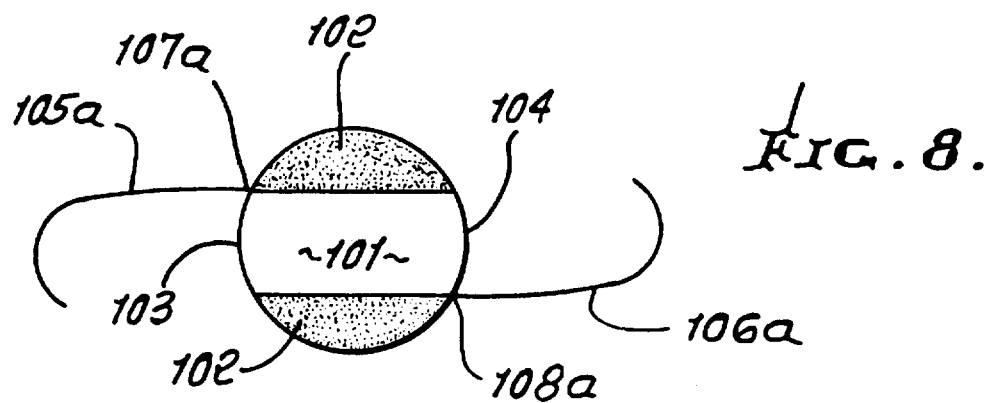
FIGS. 8–12 are plan views of various modified lenses, with darkened areas.

FIG. 8 shows a lens like that of FIG. 6; and the same parts bear the same numbers. The modified oppositely extending strand-type haptics 105a and 106a have their inner ends attached to the lens at locations 107a and 108a, the latter being at opposite ends of elongated medial transparent zone 101, adjacent light-blocking, darkened areas 102.

Figure 8A:
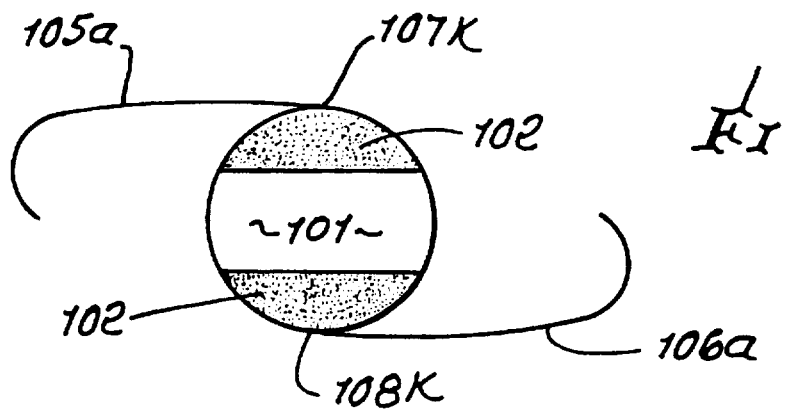

In FIG. 8a, generally like FIG. 8, the haptics' ends are attached to peripheral portions, at 107k and 108k of the lens darkened zones 102, for stability.

Figure 9:
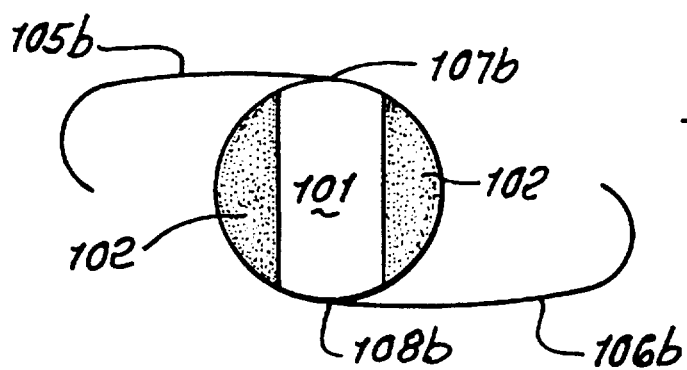

FIG. 9 shows a lens like that of FIG. 6; and the same parts bear the same numbers. The modified haptics 105b and 106b have their inner ends attached to the lens at locations 107b and 108b, the latter being at opposite ends of elongated medial transparent zone 101, tangent to opposite ends 103 and 104 of zone 101.

Figure 10:
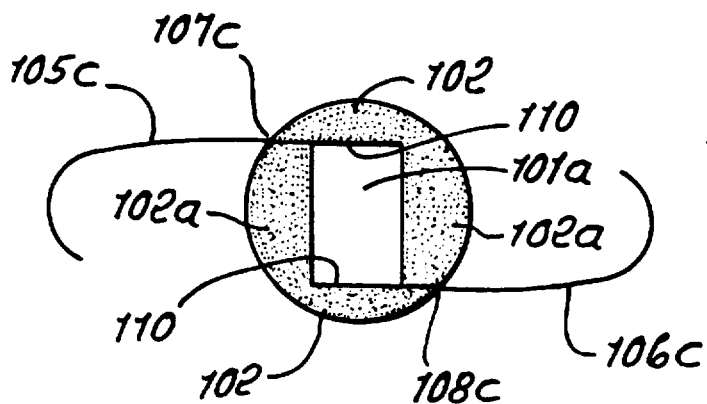

FIG. 10 shows a lens like that of FIG. 6; and the same parts bear the same numbers. There are additional darkened lens areas 102a at opposite sides of modified central rectangular transparent zone 101a, the latter surrounded by darkened zones 102 and 102a, as shown. The modified haptics 105c and 106c have their inner ends attached to the lens at locations 107c and 108c, the latter extending from opposite ends 110 of the zone 101a.

Figure 11:
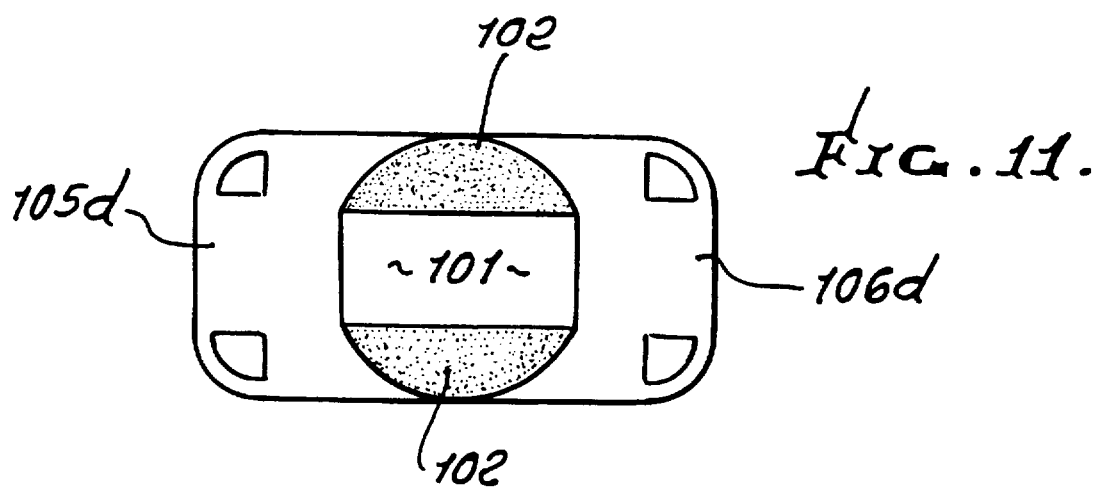
Figure 12:
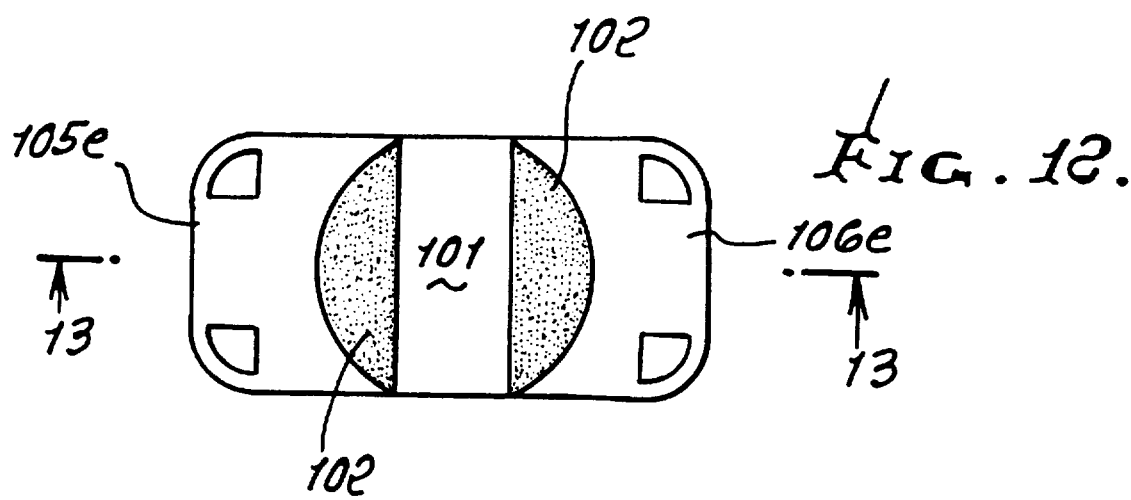
Figure 13:
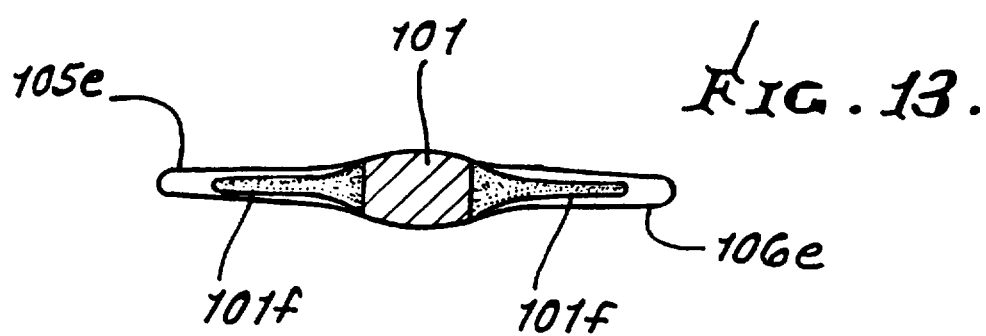
FIG. 13 is a section taken on lines 13—13 of FIG. 12.

FIGS. 11 and 12 show a lens like that of FIG. 6, wherein the same parts bear the same numbers. The modified haptics are tabular and are indicated at 105d and 106d in FIG. 11, and at 105e and 106e in FIG. 12. Haptics 105d and 106d have root ends subtending both darkened areas 102 and medial zone 101; whereas haptics 105e and 106e have root ends subtending only outer edges of darkened zones 102. Silicone substance of 101 projects into the haptics, as shown at 101f in FIG. 13.

Figure 14:
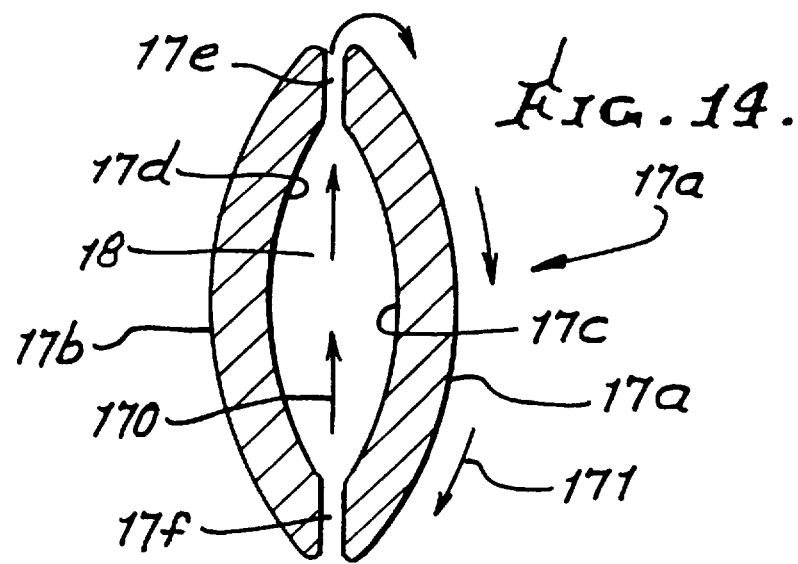
FIG. 14 is a view of a modified lens of the type seen in FIG. 3.

In FIG. 14, the lens 17a is like that of FIG. 3 and similar elements bear the same numbers. The lens differ in that it has peripheral upper and lower ports 17e and 17f, each communicating between the lens interior hollow 18 and the exterior. When placed in the eye, as in FIG. 3 or FIG. 15, fluid tends to circulate upwardly, entering space 18 via port 17f, and leaving space 18 via port 17e, due to warmer fluid rising in 18. See circulation arrows 170 and 171 within the eye. Tiny solid particles thereby are swept from the cavity 18 by fluid circulation. The lens is placed in the eye so that port 17e is upper, and port 17f is lower.

Figure 15:
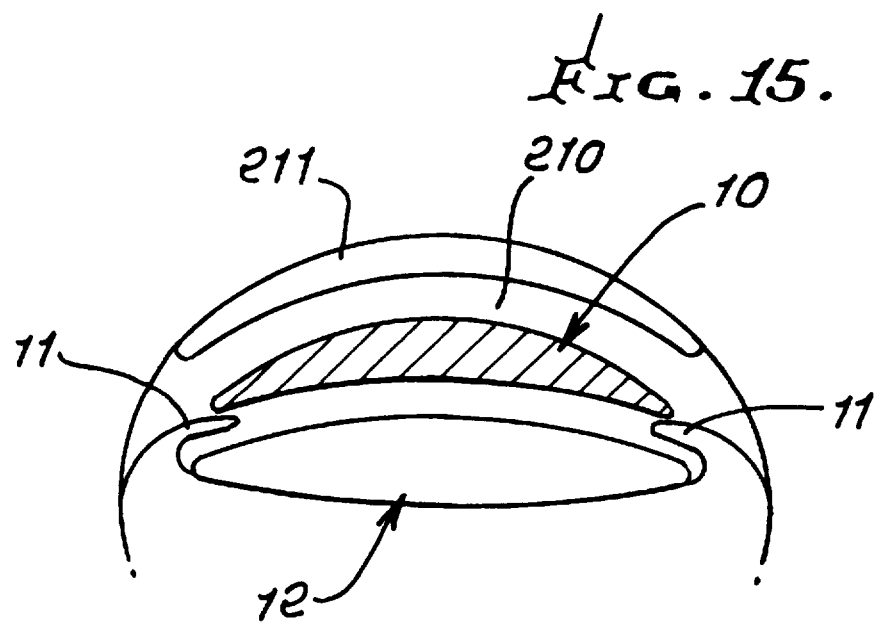
FIG. 15 is a view like FIG. 1 showing employment of the lens in the anterior chamber of the eye.

In FIG. 15, the configuration is like that of FIG. 1 except that the lens 10 is placed in the anterior cavity 210 of the eye, between the iris 11 and the dome 211 of the eye, the lens inserted via a small slit in the dome, which heals rapidly. Lens 10 and 11 cooperate to produce improved vision, lens 10 configured for that purpose. The edge of lens 10 yieldably and resiliently deforms in response to eye structure movement.

Contact lens intraocular implants may be sized at 3 by 6 mm, or 2½ by 5 mm for humans, or 4 by 7 to 6 by 10 mm, as for larger animals, such as horses. Appropriate haptics can be used, as referred to. The lenses (as with haptics) are foldable or nonfoldable, for insertion through small slits made in the eye.

I claim:

1. The method of inserting and positioning an artificial soft lens in the eye between the iris and the natural lens, that comprises:

a) providing said lens to be compliant, to have opposed surfaces, and to have a medial transparent zone and darkened border zones, the lens having an aspherical configuration, b) said lens also provided and configured to flex under pressure exerted by the iris whereby at least one of said opposed surfaces yieldably and resiliently deforms, c) and inserting said lens into the eye and positioning the lens to extend between the iris and the natural lens of the eye, and allowing said lens, including said darkened border zones, to flex under pressure exerted by the iris.

2. The method of inserting and positioning the lens of claim 1 wherein the lens medial transparent zone has a length between about 5 and 6 mm and a width between about 2.5 and 3 mm.

3. The method of inserting and positioning the lens of claim 1 including providing at least one haptic integral with said lens at an edge portion thereof.

4. The method of inserting and positioning the lens of claim 1 including providing two haptics integral with said lens at edge portions thereof.

5. The method of inserting and positioning the lens of claim 4 into the eye which includes inserting said lens between the iris and natural lens of the eye.

6. The method of inserting and positioning the lens of claim 1 in the eye which includes inserting said lens between the iris and natural lens of the eye.

7. The method of inserting and positioning the lens of claim 6 including providing haptics attached to said lens and locating said haptics under the iris and proximate thereto.

* * * * *